United States Patent
Estevez et al.

(10) Patent No.: US 10,444,203 B2
(45) Date of Patent: Oct. 15, 2019

(54) ULTRASONIC VIBRATION SENSING

(71) Applicant: Texas Instruments Incorporated, Dallas, TX (US)

(72) Inventors: Leonard William Estevez, Rockwell, TX (US); David Patrick Magee, Allen, TX (US); Amardeep Sathyanarayana, Austin, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 176 days.

(21) Appl. No.: 15/374,802

(22) Filed: Dec. 9, 2016

(65) Prior Publication Data

US 2018/0074025 A1    Mar. 15, 2018

Related U.S. Application Data

(60) Provisional application No. 62/395,060, filed on Sep. 15, 2016.

(51) Int. Cl.
*G01N 29/46* (2006.01)
*G01N 29/07* (2006.01)
*G01N 29/44* (2006.01)
*G01N 29/11* (2006.01)

(52) U.S. Cl.
CPC .......... *G01N 29/46* (2013.01); *G01N 29/075* (2013.01); *G01N 29/11* (2013.01); *G01N 29/4454* (2013.01); *G01N 2291/012* (2013.01); *G01N 2291/015* (2013.01); *G01N 2291/044* (2013.01)

(58) Field of Classification Search
CPC ...... G01N 29/46; G01N 29/075; G01N 29/24; G01N 29/4454
See application file for complete search history.

(56) References Cited

U.S. PATENT DOCUMENTS

| | | | | |
|---|---|---|---|---|
| 2,985,018 A | * | 5/1961 | Williams | G01H 9/008 367/114 |
| 3,651,687 A | * | 3/1972 | Dory | G01B 17/00 367/103 |
| 3,721,954 A | * | 3/1973 | Fontanel | G01V 1/005 367/47 |
| 3,946,377 A | * | 3/1976 | Zetting | G08B 13/1609 340/550 |

(Continued)

OTHER PUBLICATIONS

J. Tapson, "High precision, short range ultrasonic sensing by means of resonance mode-locking", Ultrasonics 199 vol. 33, No. 6, pp. 441-444, received Mar. 9, 1995, revised Jul. 6, 1995.

(Continued)

*Primary Examiner* — Helen C Kwok
(74) *Attorney, Agent, or Firm* — Michael A. Davis, Jr.; Charles A. Brill; Frank D. Cimino

(57) ABSTRACT

Mechanical vibration may be sensed by a remotely located ultrasonic sensor. An ultrasonic wave may be transmitted from a transmitter to a vibrating surface, in which the transmitter is separated from the vibrating surface by a distance. A reflected portion of the ultrasonic wave that is reflected from the vibrating surface may be received by a receiver that is also separated from the vibrating surface by a distance. A measure of phase shift amplitude in the reflected portion of the ultrasonic wave may be determined and converted into an amplitude of a vibration of the vibrating surface.

17 Claims, 6 Drawing Sheets

(56) References Cited

U.S. PATENT DOCUMENTS

| | | | | | |
|---|---|---|---|---|---|
| 4,364,264 | A * | 12/1982 | Re Fiorentin | G01B 17/08 | 367/99 |
| 4,823,601 | A * | 4/1989 | Barna | G01M 7/025 | 73/594 |
| 5,086,775 | A * | 2/1992 | Parker | G01H 9/008 | 600/438 |
| 5,099,848 | A * | 3/1992 | Parker | A61B 8/0825 | 600/441 |
| 5,251,627 | A * | 10/1993 | Morris | A61B 3/165 | 600/398 |
| 5,507,173 | A * | 4/1996 | Shearer | G01N 22/00 | 324/636 |
| 5,840,028 | A * | 11/1998 | Chubachi | A61B 8/485 | 600/437 |
| 6,041,020 | A * | 3/2000 | Caron | G01H 9/008 | 356/340 |
| 6,301,967 | B1 * | 10/2001 | Donskoy | G01N 29/045 | 73/579 |
| 6,470,749 | B1 * | 10/2002 | Han | G01B 17/02 | 73/609 |
| 7,513,160 | B2 * | 4/2009 | Lynch | G01S 15/003 | 73/599 |
| 7,850,611 | B2 * | 12/2010 | Davies | G01S 7/52028 | 600/437 |
| 8,234,923 | B2 * | 8/2012 | Ramamurthy | A61B 8/08 | 600/443 |
| 2002/0000125 | A1 * | 1/2002 | Beardmore | G01N 29/07 | 73/598 |
| 2005/0267695 | A1 * | 12/2005 | German | G01N 3/30 | 702/41 |
| 2006/0085049 | A1 * | 4/2006 | Cory | A61B 5/0536 | 607/48 |
| 2009/0012399 | A1 * | 1/2009 | Sunagawa | A61B 5/02007 | 600/454 |
| 2009/0114019 | A1 * | 5/2009 | Fatemi | G01B 17/08 | 73/587 |
| 2009/0282920 | A1 * | 11/2009 | Sato | G01H 1/00 | 73/597 |
| 2011/0063950 | A1 * | 3/2011 | Greenleaf | A61B 8/485 | 367/87 |
| 2011/0077716 | A1 * | 3/2011 | Rofougaran | G06F 19/3418 | 607/60 |
| 2011/0082383 | A1 * | 4/2011 | Cory | A61B 5/0536 | 600/547 |
| 2011/0164469 | A1 * | 7/2011 | Poggiagliolmi | G01H 9/008 | 367/94 |
| 2011/0263978 | A1 * | 10/2011 | Chen | A61B 8/48 | 600/438 |
| 2012/0130248 | A1 * | 5/2012 | Fatemi | A61B 8/06 | 600/454 |
| 2015/0301615 | A1 * | 10/2015 | Kasar | G06F 3/017 | 345/156 |
| 2016/0231153 | A1 * | 8/2016 | Rezanezhad Gatabi | G01F 1/663 | |
| 2017/0052148 | A1 * | 2/2017 | Estevez | G01S 15/10 | |
| 2017/0284859 | A1 * | 10/2017 | Bauer | G01N 29/024 | |
| 2017/0367683 | A1 * | 12/2017 | Zheng | G01S 7/52038 | |
| 2018/0231501 | A1 * | 8/2018 | Findikoglu | G01N 29/043 | |

OTHER PUBLICATIONS

Sung-Rung Huang, Robert M. Lerner, and Kevin J. Parker, "Time domain Doppler estimators of the amplitude of vibrating targets", The Journal of the Acoustical Society of America, vol. 91, No. 2, pp. 965-974, received Nov. 9, 1990, accepted Sep. 30, 1991.

"Ultrasonic transducer", Wikipedia, available at https://en.wikipedia.org/wiki/Ultrasonic_transducer on Nov. 22, 2016, pp. 1-2.

* cited by examiner

ULTRASONIC VIBRATION SENSING

CLAIM OF PRIORITY UNDER 35 U.S.C. 119 (E) PROVISIONAL

The present application claims priority to and incorporates by reference U.S. Provisional Application No. 62/395,060, filed Sep. 15, 2016, entitled "Ultrasonic Vibration Sensing,"

FIELD OF THE INVENTION

This disclosure relates to remote sensing of vibration, and in particular to the use of a remote ultrasonic transducer to sense vibration.

BACKGROUND OF THE INVENTION

There is a need to periodically monitor the health of motors and machines in order to accurately predict and schedule maintenance (or replacement) while minimizing cost and industrial production down time. Millions of industrial motors are periodically monitored today with a handheld or wired piezo accelerometer sensing device. It is estimated that the annual cost of monitoring these motors is around $300 per motor per year.

Ultrasonic vibration sensing has focused on methods in which one of the ultrasonic transducers is fixed to the vibrating surface. High frequency and relatively expensive ultrasonic transducers are used. These systems may require on-site calibration and may not consider practical aspects of deployment such as heat conduction from the vibrating surface which may prevent the transducer from operating correctly.

BRIEF DESCRIPTION OF THE DRAWINGS

Particular embodiments in accordance with the invention will now be described, by way of example only, and with reference to the accompanying drawings.

Figure 1:
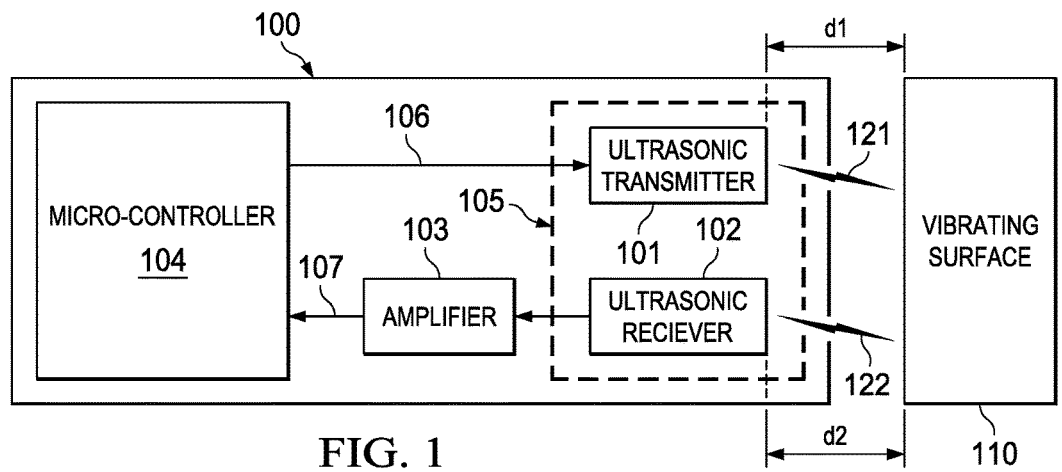
FIG. 1 is a block diagram of an example system for measuring vibration using a remote ultrasonic transducer.

Other features of the present embodiments will be apparent from the accompanying drawings and from the detailed description that follows.

DETAILED DESCRIPTION OF EMBODIMENTS OF THE DISCLOSURE

Specific embodiments of the disclosure will now be described in detail with reference to the accompanying figures. Like elements in the various figures are denoted by like reference numerals for consistency. In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Recent advancements in ultra-low power processing technologies and low cost ultrasonic transducers have enabled the development and deployment of small and low cost coin cell operated wireless motor monitors with greater than ten years of battery life. Although these systems do not provide the same broadband sensitivity of the existing handheld systems, they can serve as a non-contact triage system to locally capture and analyze machine vibration signatures. The combination of low power ultrasonic signaling and processing enables these systems to be deployed in small and difficult to reach motor/machine monitoring locations and to pay for themselves within a few months of operation. Since ultrasonic transducers are sensitive to audio at higher frequencies, lower cost ultrasonic transducer platforms may be limited to vibration displacements up to 0.5 micron and a vibration frequency range of 0 to 800 Hz, for example.

Ultrasonic transducers are commonly used in industrial ranging and flow metering applications to determine changing distances, levels, and flows. These applications commonly use either a time of flight or a phase based approach.

In a time of flight approach, a pulse is sent from an ultrasonic transducer and the time elapsed before receiving the reflection is measured. While this approach is good for absolute distance or flow measurements, it is not suitable for measuring high frequency vibrations because cross-talk between return responses from individual pulses makes it impossible to accurately determine exactly when the response of a given transmitted pulse has been received.

A continuous phase based approach as disclosed herein may be used to remotely sense vibration since correlation between the transmitted and received pulse train is not required. In a continuous phase based approach, a series of pulses is continuously sent from an ultrasonic transducer and variations in the phase of the reflected pulses received by another ultrasonic transducer are measured. This approach enables measurement of higher frequency signatures, as will be disclosed herein.

FIG. 1 is a block diagram of an example system 100 for measuring vibration using a remote ultrasonic transducer. An Ultrasonic Vibration Sensing System (UVSS) comprises four key components: a micro-controller 104, an amplifier 103, an ultrasonic transmitter 101, and an ultrasonic receiver 102. Ultrasonic transmitter 101 and ultrasonic receiver 102 may be implemented as a single ultrasonic transceiver 105, for example. The UVSS may be located "remotely" from a vibrating surface 110 to allow sensing of vibration without being exposed to excessive heat or vibration produced by the vibrating surface.

The general operation of ultrasonic transceivers is well known; see for example "Ultrasonic Transducer," Wikipedia, updated 25 Oct. 2016. Ultrasonic transducers are transducers that convert ultrasound waves to electrical signals or vice versa. Many ultrasound sensors may be transceivers because they can both sense and transmit. These devices work on a principle similar to that of transducers used in radar and sonar systems, which evaluate attributes of a target by interpreting the echoes from radio or sound waves, respectively. Active ultrasonic sensors generate high-frequency sound waves and evaluate the echo which is received back by the sensor, measuring the time interval between sending the signal and receiving the echo to determine the distance to an object. Ultrasonic sensors are now widely used in cars as parking sensors to aid the driver in reversing into parking spaces, for example.

Typical ultrasonic transducers are piezoelectric transducers or capacitive transducers. Piezoelectric crystals change size and shape when a voltage is applied; AC voltage makes them oscillate at the same frequency and produce ultrasonic sound. Since piezoelectric materials generate a voltage when force is applied to them, they can also work as ultrasonic detectors. Some systems use separate transmitters and receivers, while others combine both functions into a single piezoelectric transceiver.

Capacitive transducers use electrostatic fields between a conductive diaphragm and a backing plate. A capacitor ("condenser") microphone has a thin diaphragm that responds to ultrasound waves. Changes in the electric field between the diaphragm and a closely spaced backing plate convert sound signals to electric currents, which can be amplified.

Ultrasound transmitters can also use non-piezoelectric principles such as magnetostriction. Materials with this property change size slightly when exposed to a magnetic field, and make practical transducers.

The beam pattern of a transducer can be determined by the active transducer area and shape, the ultrasound wavelength, and the sound velocity of the propagation medium.

Referring still to FIG. 1, ultrasonic transmitter 101 may be positioned to transmit a signal 121 towards a vibrating surface 110. Vibrating surface 110 may be part of a machine that has moving parts, such as a motor, for example. In a motor, rotation of a rotor may cause a vibration due to an unbalance in the rotor, wear in the bearings, time varying load on the motor, etc. In other applications, vibrating surface 110 may be part of a wall or column of a building, for example. Vibrating surface 110 may be part of a vehicle, such as an automobile, truck, train, plane, etc. Vibrating surface 110 may be part of a machine or type of device used in industrial, commercial, residential, etc. locations, for example.

A reflected ultrasound signal 122 may be received by ultrasound receiver 102. As mentioned above, ultrasound transmitter 101 and ultrasound receiver 102 may be two separate devices, or may be a single device 105 that performs both transmission and reception. In the case of separate devices, transmitter 101 may be separated from vibrating surface 110 by a distance d1. Similarly, receiver 102 may be separated from vibrating surface 110 by a distance d2, which may be the same or different from d1. In the case that transmitter 101 and receiver 102 are implemented in a single device 105, then distance d1 may be the same as distance d2.

An ultrasound signal may be produced by receiver 102 in response to reflected signal 122 and provided to amplifier 103. Amplified signal 107 may then be processed by microcontroller 104. Microcontroller 106 may also produce signal 106 that is provided to ultrasonic transmitter 101 to produce transmitted signal 121.

Reflected signal 122 will have a phase shift in time in response to the displacement of the vibrating surface 110. A time of flight from the transmitter to the vibrating surface and back to the receiver is referred to herein as "channel delay." Channel delay may be represented by equation (1).

$$d(t) = A \times \sin(\omega t + \varphi) + B \quad (1)$$

where:
d is the channel delay (sec),
A is the amplitude (sec), determined by a calibration procedure,
B is the bias in the delay (sec),
$\omega$ is the excitation frequency (rad/sec),
$\varphi$ is the phase offset (rad), and
t is the time (sec).

The magnitude of the time varying signal corresponds to a voltage which is generated in response to an ultrasonic signal. That energy is a function of distance, temperature, sensitivity, amplification of the signal, etc. It should to be correlated to a known physical displacement and vibrating fundamental frequency of the surface of interest.

The calibration procedure is straightforward. A vibrating surface of a known peak-to-peak displacement level may be selected. A handheld accelerometer may be used to measure the peak-to-peak displacement of the selected surface, for example. The peak-to-peak voltage level from the transducer may then be measured and a scale factor (mm/V or u/V) may be determined based on the measured peak-to-peak displacement of the selected surface. A detailed description of a calibration procedure is described later in this disclosure.

The bias here represents the time of flight for the ultrasonic wave to be reflected from a non-vibrating surface. The sinusoidal component is the result of small displacements due to the surface vibration of vibrating surface 110.

While not illustrated in FIG. 1, sensor 100 may also include an interface to send vibration data to a remote host, for example. The interface may provide a hard wired interface for a serial or parallel communication link using known or later developed communication standards, such as RS-232, etc. Alternatively, the interface may provide a wireless interface that conforms to a known or later developed wireless communication protocol, such as Bluetooth, Wi-Fi (IEEE 802.11), cellular, etc.

Figure 2:
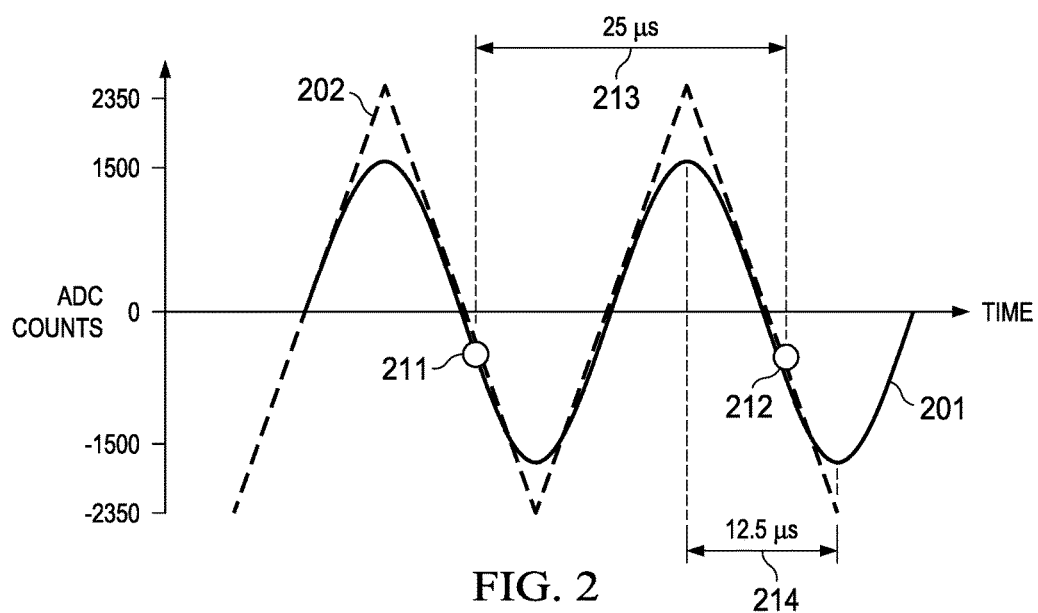
FIG. 2 is a plot illustrating subNyquist sampling of a reflected ultrasonic signal.

FIG. 2 is a plot illustrating subNyquist sampling of a reflected ultrasonic signal, such as signal 122 in FIG. 1. The variations in channel delay may be sensed by ultrasonic receiver 102 as changes in phase of the reflected signal. By sampling at subNyquist rate near the zero crossing region of the reflected ultrasonic wave, the vibration signal may be reconstructed. In this example, subNyquist sampling is performed once per cycle, as indicated at 211, 212. Sampling in the region of the zero crossing provides accurate results.

In the example system of FIG. 1, microcontroller 104 includes an analog to digital converter (ADC). For this example, it is assumed that the ADC is a 12 bit ADC capable of producing a digital value in the range of +/−2048 in response to signal 107 received from amplifier 103. For purposes of the following explanations, the output of the ADC will be referred to as "ADC counts". In this example, the ultrasonic signal generated by transmitter 101 has a frequency of 40 kHz, which has a period of 25 us. Thus, sample points 211, 212 are approximately 25 us apart, but distance 213 will vary slightly in response to vibration of surface 110 causing a phase change in reflected signal 122.

As depicted in FIG. 2, for a sinusoidal signal 201 with a peak to peak amplitude of around 3000 ADC counts, the zero crossing region can be linearized to form a triangular wave 202 by assuming that the magnitude scaling between the triangle signal and the sinusoidal signal is (pi/2)*peak-to-peak amplitude of the received sinusoidal signal 201. In this example, sinusoidal signal 202 has a peak-to-peak amplitude of approximately 3000 ADC counts, and triangular wave 202 therefore has a peak-to-peak value of approximately 4700 ADC counts in this example.

Figure 3:
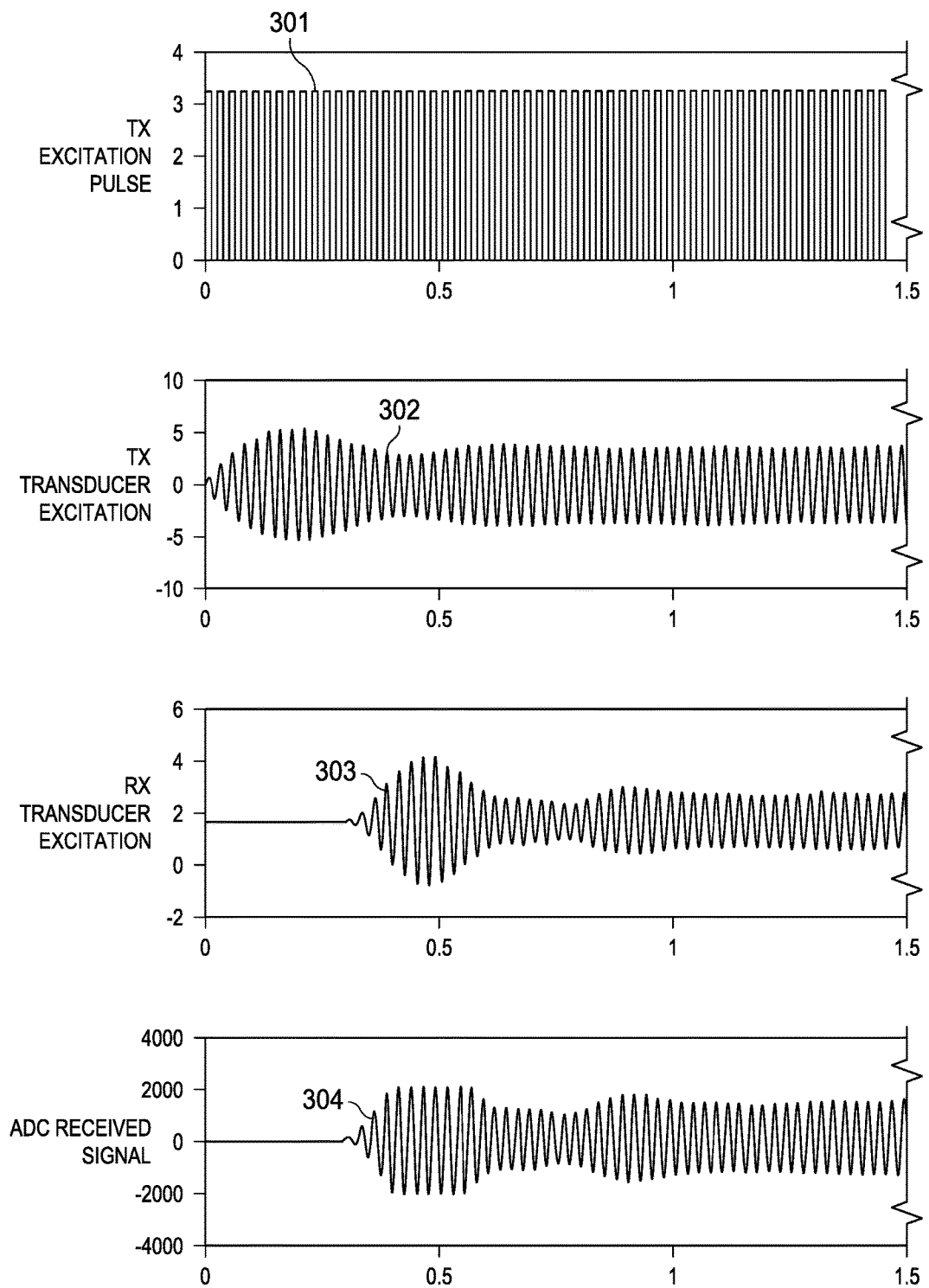
FIG. 3 is set of plots illustrating operation of the remote ultrasonic transducer of FIG. 1.

FIG. 3 depicts a Matlab simulation of a reflected ultrasonic signal with a time varying channel delay as described above. A pulse train 301 is first generated to excite the ultrasonic transmitter (TX) 101, referring back to FIG. 1. As mentioned above, pulse train 301 may be produced by microcontroller 104 and provided to ultrasonic transmitter 101 which then produces transmitted excitation signal 302. After the time of flight required to make a round trip from the reflecting surface has passed, the receiver (RX) transducer 102 begins to resonate and produces RX excitation signal 303, which may then be amplified and sampled using an ADC to form digitized received signal 304.

Figure 4A:
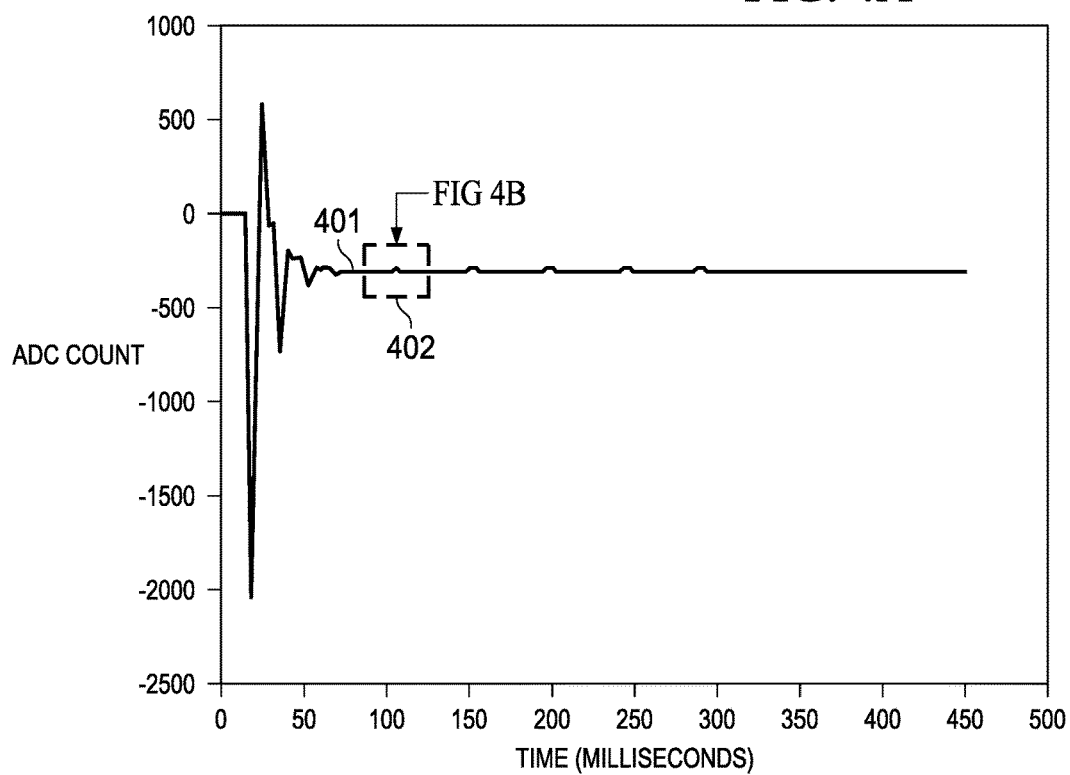
FIGS. 4A and 4B illustrate sampled data taken from a reflected ultrasonic wave.
Figure 4B:
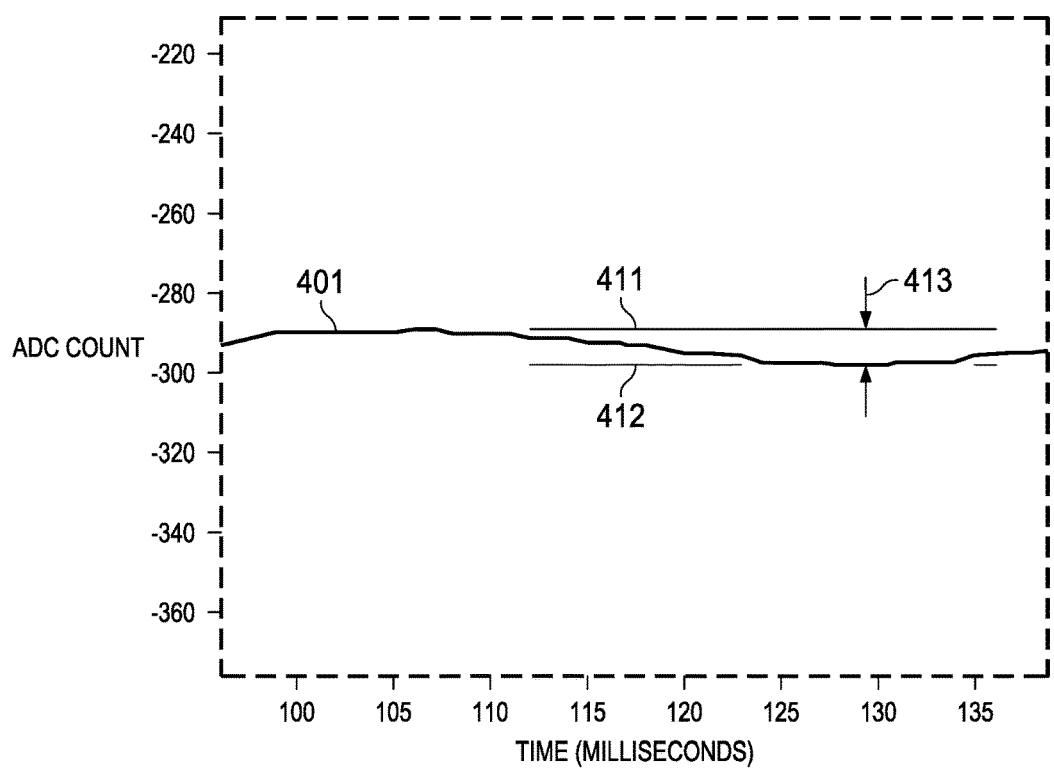
Figure 5:
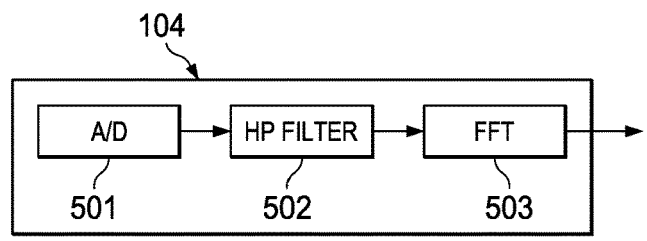
FIGS. 5, 6A, 6B and 6C illustrate processing performed by the system of FIG. 1.

FIGS. 4A and 4B illustrate sampled data 401 taken from a reflected ultrasonic wave, such as wave 304 in FIG. 3. After the transients in the initial excitation of the receiving transducer have settled, the phase and amplitude of the vibrating surface can be extracted from a window 402 of data illustrated in FIG. 4A, for example. Window 402 is illustrated in more detail in FIG. 4B. Notice in this example that the reflected signal is being sampled in the region of −300 ADC counts, which is just a little below the zero crossing point. Notice that the sampled magnitude is varying between approximately −290 ADC counts indicated at 411 and −300 ADC counts indicated at 412, for a peak-to-peak value 413 of approximately 10 ADC counts.

Referring again to FIG. 2, the magnitude of variations in the phase can be determined by first evaluating the magnitudes of the triangle signal and the received sinusoid. This magnitude ratio is determined to be approximately 1.6× the peak-to-peak magnitude over a quarter wavelength 214 of the received signal. A phase shift of a half wavelength relates to physical displacement as shown in equation (2).

$$\lambda = c/f = c \times T \quad (2)$$

Where:
$\lambda$ is the wavelength (m),
c is the speed of sound (m/sec),
f is the frequency (Hz), and
T is the period (sec)

For a 40 kHz ultrasonic signal at 25° C. a half wavelength=4.25 mm. For a signal 202 with a linearized peak-to-peak magnitude of 4700 ADC counts, variations of 1 ADC count would correspond to physical displacements of 0.9 micron, as shown in equation (3).

$$0.00425 \text{ meters}/4700 \text{ counts} = 0.9 \text{ micron/count} \quad (3)$$

Referring again to FIG. 4B, since the magnitude of the subNyquist sample has a peak-to-peak value of approximately 10 ADC counts; the magnitude of the vibration illustrated in FIG. 4B is approximately 9 microns peak-to-peak, according to equation 3.

In some embodiments, a time of flight measurement may be periodically taken to measure and subsequently account for changes in temperature for equation (2). The speed of sound (c) is dependent on the temperature of the air through which the sound wave travels.

Figure 6A:
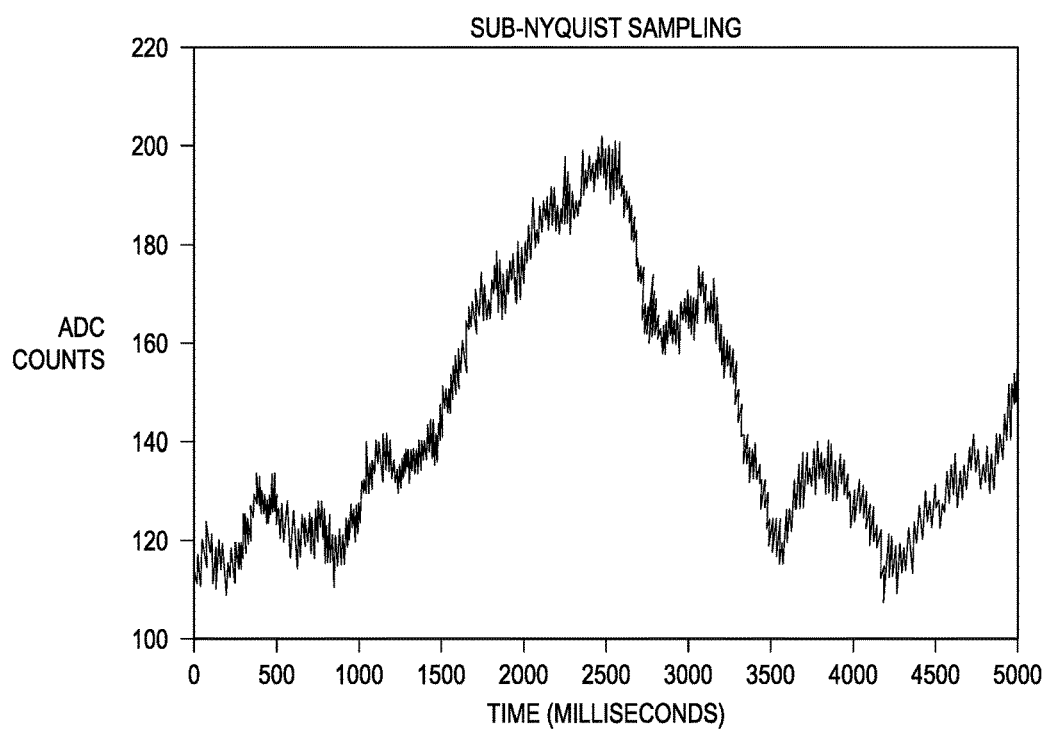
Figure 6B:
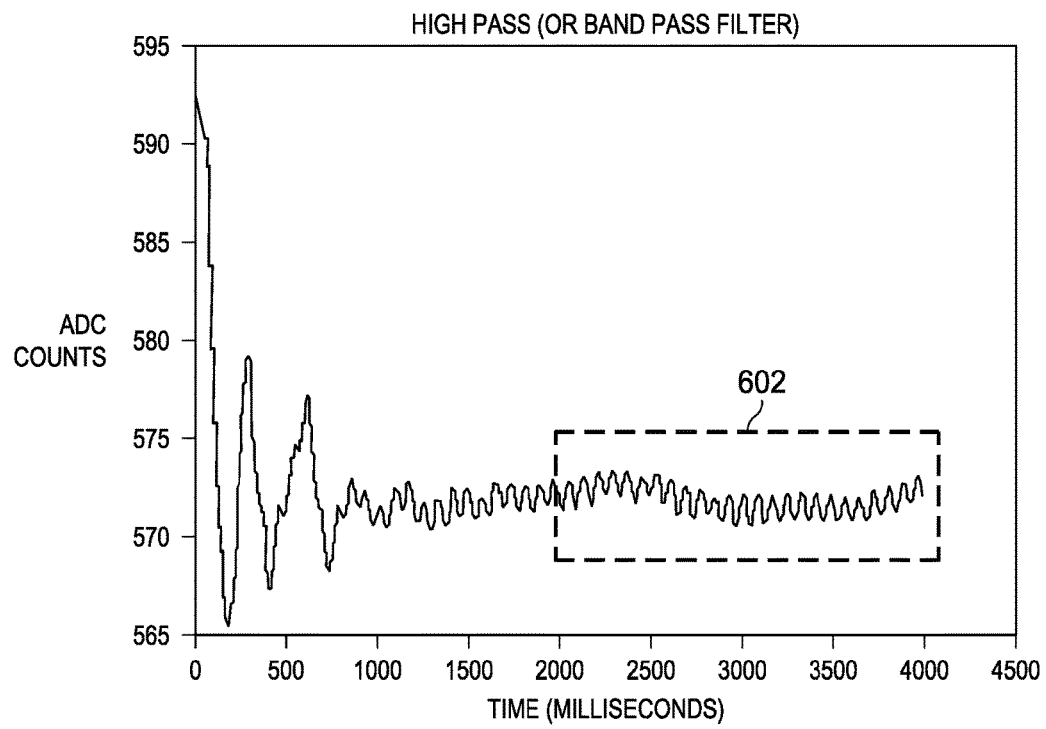

FIGS. 5, 6A, 6B, and 6C illustrate processing performed by the system of FIG. 1. The phase signal is first extracted by sampling the ultrasonic reflection near the zero crossing as previously described using an ADC function 501 to produce a subNyquist sampled signal is illustrated in FIG. 6A. ADC function 501 may be performed by an ADC included within microcontroller 104. The signal may then be high pass filtered using a filter function 502 to remove low frequency interferences, such as 60 Hz (which corresponds to AC line noise in the US), to produce a filtered signal as illustrated in FIG. 6B. HP filter function 502 may be performed using known or later developed digital signal processing (DSP) techniques executed on microcontroller 104, referring again to FIG. 1, for example.

Figure 6C:
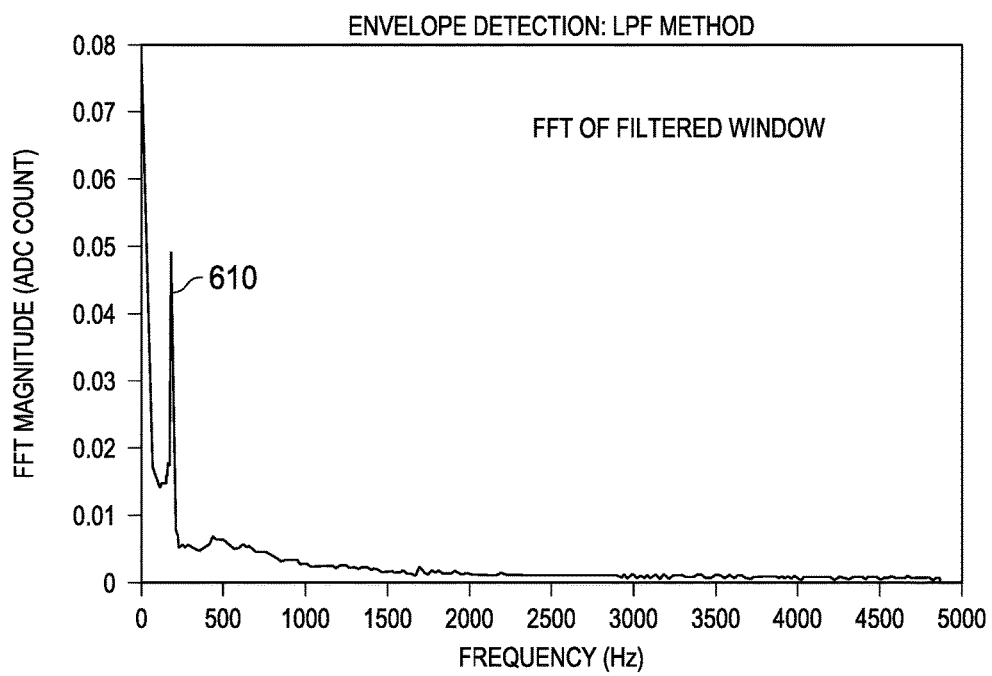

A window of data 602 may be selected for further analysis by applying a Fast Fourier Transform (FFT) 503 to the windowed region 602 in which transients of the receiving ultrasonic transducer have settled down. FFT function 503 may be performed using known or later developed DSP techniques executed on microcontroller 104, for example. FIG. 6C illustrates the result of the FFT function in this example. A peak 610 at approximately 200 Hz indicates the vibration has a frequency of approximately 200 Hz.

In some embodiments, the FFT transform may be performed to extract frequency components of the sensed vibration and track their amplitudes over time.

Figure 7:
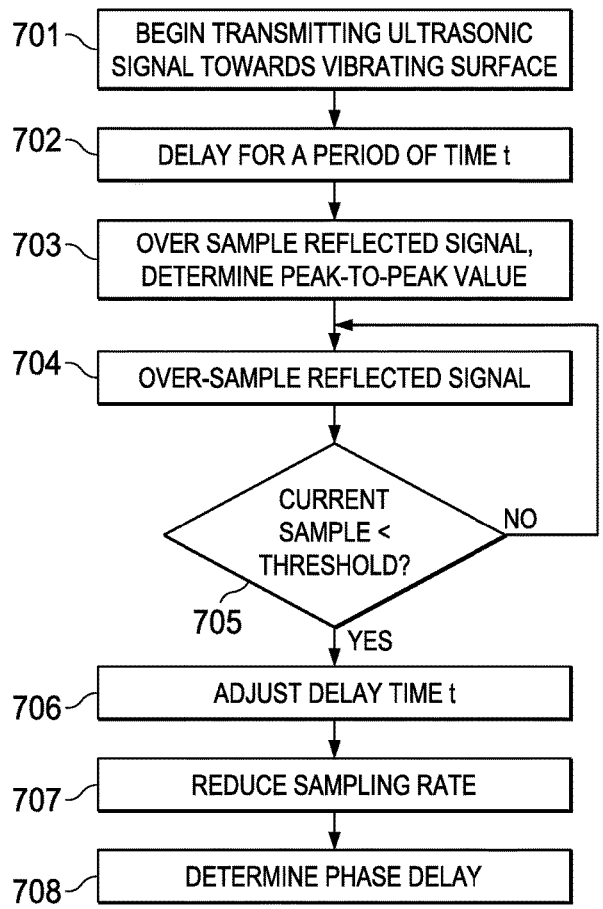
FIGS. 7 and 8 are flow charts illustrating methods for determining a zero crossing region during sampling.

FIG. 7 is a flow chart illustrating a method for determining a zero crossing region during sampling. As described above with regard to FIG. 1, the excitation pulses for the transmitting transducer may be generated by the same micro-controller 104 which captures the receiving transducer's electrical signals. Microcontroller 104 may be configured to adjust the delay in analog to digital conversion until averaged values are near zero.

At step 701, the microcontroller 104 may send an excitation sequence to transmitter 101 to begin transmitting a sequence of ultrasonic pulses, such as illustrated in FIG. 3.

As illustrated by 303 in FIG. 3, there will be a delay in the RX excitation due to the channel delay. There may also be an initial transient response. A timer or other means may be used by microcontroller 104 in step 702 to delay the start of sampling of the reflected ultrasonic signal by a time delay "t" so that sampling occurs during a steady-state region of the reflected signal in order to save power, for example. An initial value of t may be selected based on past experience, or a pre-defined application parameter, etc.

After the delay period, microcontroller 104 may instruct the ADC function 501 (see FIG. 5) to begin sampling at an oversample rate in step 703. A peak to peak value of the received ultrasonic signal may be determined after sampling one or more cycles of the received ultrasonic signal. The oversample rate may be selected to be eight times (8×) the resonant frequency of the receiver transducer in order to get a reasonably accurate peak to peak value, for example. In another embodiment, the oversample rate may be higher or lower than 8× in a tradeoff of accuracy and power consumption.

After determining the peak to peak value, oversampling may continue in step 704 at the same oversample rate, or at a revised rate.

Each sample may be compared to the peak to peak value in step 705 to determine if the current value is less than a threshold value. For example, the threshold value may be selected to be approximately ⅛ of the peak to peak value. Steps 704 and 705 may be repeated until the current sample falls below the threshold value. At this point in time, it may be assumed that the sampling is being performed in the zero crossing region.

At step 706, the delay time used in step 702 may be adjusted to be equal to the current timer value and stored for use the next time the process is repeated.

At step 707, the sample rate may be reduced to a subNyquist rate. In this embodiment, sampling is performed at the resonant frequency. If the resonant frequency of the receiver is 40 kHz, then sample may be performed at 40 kHz, for example.

At step 708, a phase angle signal may be extracted as described in more detail with reference to FIGS. 5, 6A-6C.

Figure 8:
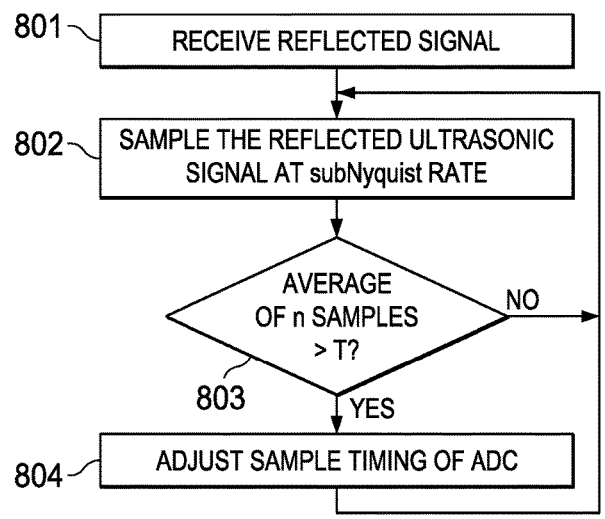

FIG. 8 is a flow chart illustrating another method for determining a zero crossing region during sampling. As described above with regard to FIG. 1, the excitation pulses for the transmitting transducer may be generated by the same micro-controller 104 which captures the receiving transducer's electrical signals. Microcontroller 104 may be configured to adjust the delay in analog to digital conversion until averaged values are near zero.

At step 801, an ultrasonic signal 122 of FIG. 1 that is reflected from a vibrating surface is received by receiver 102 of FIG. 1.

An ADC function is performed by microcontroller 104 as a subNyquist rate. In this example, the ultrasonic signal has a frequency of 40 kHz, and the reflected signal 122 is sampled at a rate of 40 kHz in step 802

A running average of the sample magnitudes is taken over a number of samples. If the running average is approximately zero at step 803, then the sampling continues at step 802. However, if the running average is greater than zero by a threshold value T, then the timing of the ADC sampling is adjusted at step 804. After several loops of timing adjustment, the ADC sampling time should settle with no more adjustments needed for a period of time. The magnitude T of the threshold value may be selected to control how near the zero crossing the sampling is performed.

The method described in FIG. 8 may be performed to maintain sampling in the zero crossing region after initially determining the zero crossing region using the method of FIG. 7, for example.

System Example

Figure 9:
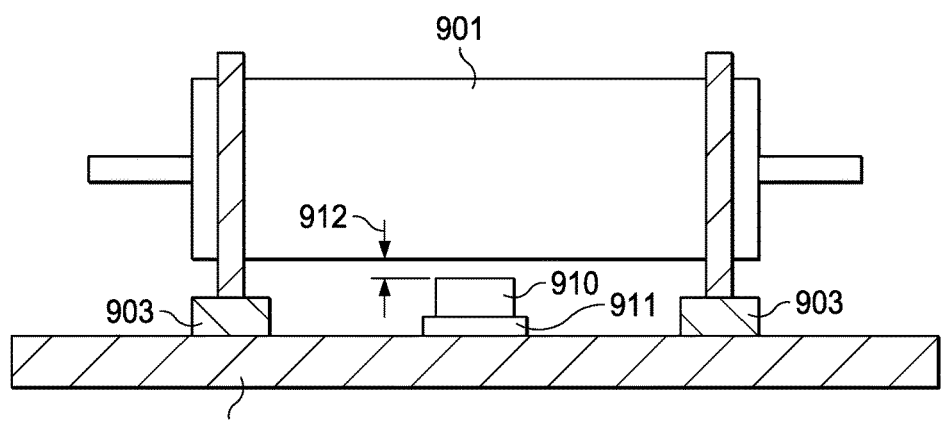
FIG. 9 illustrates an example application of an ultrasonic vibration sensing system.

FIG. 9 illustrates an example application of an ultrasonic vibration sensing system. In this example, a motor 901 is mounted on a stable surface 902, such as the floor of a building, or the frame of a machine, for example. Mounting blocks 903 may secure the motor to the stable surface.

Ultrasonic vibration sensing system 910 may also be mounted on stable surface 902. Ultrasonic vibration sensing system 910 may be similar to system 100 described with regard to FIG. 1, for example. In some cases, a vibration damping material 911 may be positioned between sensing system 910 and stable surface 902 in order to reduce sensing of vibration that may be occurring in stable surface 902.

As discussed above, sensor system 910 may be located remotely from motor 901 and separated by a distance 912. Experiments have shown that a separation 912 of as much as 13 cm or more may be accommodated using an inexpensive 40 kHz ultrasonic transducer using the phase detection techniques described herein. This configuration allows the electronics in sensor 910 to be separated from and protected from heat produced by motor 901.

Based on lab experiments, the described method is capable of resolving displacements of 0.5 microns at frequencies from 0 to 800 Hz using a low cost transducer. The frequency limitation is due to audio sensitivities of these transducers at higher frequencies. Low cost transceivers operating at 40 kHz, for example, produce good results in environments in which loud audio (i.e. 93 dbA) is not present at these higher frequencies.

For higher frequency transducers, such as more expensive units that operate at 400 kHz, for example, audio sensitivities do not interfere with the reflected phase signal until higher frequencies are present, such as 2 kHz, thus enabling higher frequency sensing.

An advantage in the disclosed method versus previous work is in the decoupling of the transmitted and received signal for extracting the phase signal. This approach greatly reduces the required processing and power.

The disclosed approach may also be used in a physical configuration in which the transmitter or the receiver is attached to the vibrating surface. This configuration may provide a much better signal to noise ratio (SNR)/sensitivity since reflections from multiple surfaces would not be an issue. The anticipated resolution for this implementation would be an order of magnitude better (0.05 microns instead of 0.5 microns). However, the benefit of non-contact sensing would be lost since this design would then be a contact sensor. Non-contact vibration sensing eliminates requirements for tightly coupled/shock proof/high temperature electronics.

Non-contact vibration sensing enables scanning of multiple surfaces with a single sensor.

The disclosed method eliminates synchronization and processing required to extract the phase signal. It also enables lower cost implementations since a minimal amount of memory and processing is required.

Memory requirements may be reduced further by sampling at a lower multiple of the Nyquist frequency (Nyquist/X, where X is an integer). The Nyquist frequency for a given ultrasound transducer is defined to be twice the fundamental frequency of the transducer. For example, the method described above may be performed in which the system first samples at Nyquist/2 to determine what the highest frequency components of the system are. The method may then reduce sampling to Nyquist/4, Nyquist/8, etc. to minimize the power, processing, and memory requirements.

Calibration Procedure

The disclosed approach may require a calibration procedure to convert the magnitude of the ultrasonic vibration signal to a physical displacement. The magnitude of the reflected vibration signal depends on the strength of the transmitted signal, distance from the reflected signal, and the temperature of the conducting air. The sensor should therefore be pre-calibrated over its operating temperature, distance, and transmitting intensity with these calibration settings stored in a nonvolatile memory that may be included with the sensor.

This calibration process may be conducted at deployment or in the factory, hi a factory environment, known vibrational displacements over the operating range of temperatures and sensing distances may be recorded in a look up table stored in nonvolatile memory within the sensor from which the sensor subsequently references when deployed.

In a field based method, a calibrated sensor may be used in conjunction with the deployed sensor (i.e. an accelerometer) to provide ground truth information while the machine of interest is cycled through various representative operating states with varied air temperatures. For example, a heat gun may be used to heat the air temperature over the range of anticipated operating temperatures.

Information from other sensors monitoring the same machine may also be leveraged when wireless deployment of multiple sensors on the same machine or vibrating structure are used. In this method, recently measured vibrations at various locations on the machine may be used along with Time of Flight (TOF) measurements. TOF measurements may be used to calibrate for distance when temperature is known or for temperature when the distance is known/fixed.

The magnitude of various frequency components of interest may vary across a vibrating machine or structure. A wireless ultrasonic vibration sensing system may leverage this information for calibration during field deployment. In this case, accelerometer based measurements may be taken as each sensor is deployed and either the ambient temperature or distance and transmission power may be determined for each sensor. Accelerometer vibration measurement data for known locations on the machine may then be used to calibrate each sensor by either sharing reflected ultrasonic magnitudes at frequencies of interest between sensors or physically moving each sensor for a short period of time across a variety of locations with known vibrational characteristics (but different magnitudes) before permanently installing each sensor in one location. Data sharing may be performed using a wireless interface that may be included with each sensor, for example.

Each ultrasonic vibration sensor may also be calibrated for transducer efficiency and sensitivity. This calibration may be conducted at the factory by simply adjusting the Pulse width of the excitation pulse until comparable results are seen between transducer pairs. The best resonant frequency of the transducer pair may also be determined by sweeping the specified resonant frequency range over a limited range to find the maximum response.

Since the optimal Tx power for a transducer pair in a given environment is dependent on various factors, a method for determining an optimized Tx power/phase for a given distance and air temperature may be performed using the following steps.

In a first step, the Tx power may be increased by increasing duty cycle of the PWM signal until of a reflected ultrasonic signal can be sensed from a steady state vibrating surface.

In a next step, a TOF measurement may be taken to ensure the distance is within the anticipated range.

In a next step, the phase of the signal may be adjusted until samples can be averaged around zero.

In a next step, repeated measurements at this Tx power may be taken and a standard deviation may be calculated.

In a next step, the Tx power may be increased by a selected amount and the above steps repeated to calculate a second standard deviation. If the standard deviation does not increase significantly, the above steps may be repeated. If the standard deviation does increase significantly, then go back to the previous Tx power and store as optimal.

Other Embodiments

While the invention has been described with reference to illustrative embodiments, this description is not intended to be construed in a limiting sense. Various other embodiments of the invention will be apparent to persons skilled in the art upon reference to this description. For example, a sensor such as described in FIG. 1 may be used to sense vibration in all manner of machines, vehicles, and structures in industrial, commercial, medical, and residential applications, for example.

The techniques described in this disclosure may be implemented in hardware, software, firmware, or any combination thereof. If implemented in software, the software may be executed in one or more processors, such as a microprocessor, application specific integrated circuit (ASIC), field programmable gate array (FPGA), or digital signal processor (DSP). The software that executes the techniques may be initially stored in a computer-readable medium such as compact disc (CD), a diskette, a tape, a file, memory, or any other computer readable storage device and then loaded and executed in the processor. In some cases, the software may also be sold in a computer program product, which includes the computer-readable medium and packaging materials for the computer-readable medium. In some cases, the software instructions may be distributed via removable computer readable media (e.g., floppy disk, optical disk, flash memory, USB key), via a transmission path from computer readable media on another digital system, etc.

Certain terms are used throughout the description and the claims to refer to particular system components. As one skilled in the art will appreciate, components in digital systems may be referred to by different names and/or may be combined in ways not shown herein without departing from the described functionality. This document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" and derivatives thereof are intended to mean an indirect, direct, optical, and/or wireless electrical connection. Thus, if a first device couples to a second device, that connection may be through a direct electrical connection, through an indirect electrical connection via other devices and connections, through an optical electrical connection, and/or through a wireless electrical connection.

Although method steps may be presented and described herein in a sequential fashion, one or more of the steps shown and described may be omitted, repeated, performed concurrently, and/or performed in a different order than the order shown in the figures and/or described herein. Accordingly, embodiments of the invention should not be considered limited to the specific ordering of steps shown in the figures and/or described herein.

It is therefore contemplated that the appended claims will cover any such modifications of the embodiments as fall within the true scope and spirit of the invention.

What is claimed is:

1. A method for sensing vibration ultrasonically, the method comprising:
    transmitting an ultrasonic wave from a transmitter to a vibrating surface, in which the transmitter is separated from the vibrating surface by a first distance;
    receiving a reflected portion of the ultrasonic wave that is reflected from the vibrating surface by a receiver that is separated from the vibrating surface by a second distance;
    sampling the reflected portion of the ultrasonic wave at a sub-Nyquist rate in a zero-crossing region of the reflected portion of the ultrasonic wave to produce a set of samples;
    determining an amplitude of a frequency component of the set of samples; and
    converting the amplitude of the frequency component into an amplitude of a vibration of the vibrating surface.

2. The method of claim 1, in which the sub-Nyquist rate is Nyquist/2, where Nyquist is twice a fundamental frequency of the ultrasonic wave.

3. The method of claim 2, in which the sub-Nyquist rate is Nyquist/2 for a first period of time, and is then reduced to Nyquist/n for a second period of time, where n is an integer greater than 2.

4. The method of claim 2, in which the processing the set of samples includes:
    filtering the set of samples with a high pass filter to produce a filtered set of samples; and
    performing an FFT on the filtered set of samples to determine a frequency of the frequency component of the set of samples.

5. The method of claim 1, further including adjusting a time for sampling the reflected portion of the ultrasonic wave such that an average amplitude of the set of samples is less than a threshold value.

6. The method of claim 1, in which the converting the measure of phase shift amplitude into an amplitude of vibration includes calculating a phase shift displacement based on a wavelength of the reflected portion of the ultrasonic wave and a magnitude scale factor between a triangle approximation signal and the reflected portion of the ultrasonic wave in a zero crossing region.

7. The method of claim 6, further including determining a time of flight for the reflected portion of the ultrasonic wave; and using the time of flight to determine a wavelength of the reflected portion of the ultrasonic wave.

8. The method of claim 1, in which the transmitter and the receiver are collocated in a transducer, such that the first distance is the same as the second distance.

9. The method of claim 1, in which the transmitter and the receiver are mounted on a surface separated from the vibrating surface.

10. A system for sensing vibration ultrasonically comprising:
   a transmitter configured to transmit an ultrasonic wave to a vibrating surface, in which the transmitter is separated from the vibrating surface by a first distance;
   a receiver configured to receive a reflected portion of the ultrasonic wave that is reflected from the vibrating surface, in which the receiver is separated from the vibrating surface by a second distance; and
   processing logic coupled to the receiver, the processing logic configured to:
   sample the reflected portion of the ultrasonic wave at a sub-Nyquist rate in a zero-crossing region of the reflected portion of the ultrasonic wave to produce a set of samples;
   determine an amplitude of a frequency component of the set of samples; and
   convert the amplitude of the frequency component into an amplitude of a vibration of the vibrating surface.

11. The system of claim 10, in which the processing logic includes an analog to digital converter configured to sample the reflected portion of the ultrasonic wave at a sub-Nyquist rate to produce the set of samples for use by the processing logic to determine the amplitude of the vibration of the vibrating surface.

12. The system of claim 11, in which the sub-Nyquist rate is Nyquist/2, where Nyquist is twice a fundamental frequency of the ultrasonic wave.

13. The system of claim 11, in which the sub-Nyquist rate is Nyquist/2 for a first period of time, and is then reduced to Nyquist/n for a second period of time, where n is greater than 2.

14. The system of claim 11, in which the processing logic is configured to adjust a time for sampling the reflected portion of the ultrasonic wave such that an average amplitude of the set of samples is less than a threshold value.

15. The system of claim 10, in which the processing logic is further configured to convert the amplitude of the frequency component into an amplitude of vibration by calculating a phase shift displacement based on a wavelength of the reflected portion of the ultrasonic wave and a magnitude scale factor between a triangle approximation signal and the reflected portion of the ultrasonic wave in a zero crossing region.

16. A system comprising:
   a device having at least one rotating component included within a housing;
   an ultrasonic vibration sensor mounted on a stable surface, such that a sensing region of the sensor is separated from the housing by a distance, in which the sensor includes:
   a transmitter configured to transmit an ultrasonic wave to a surface of the housing of the device, in which the transmitter is separated from the surface of the housing by a first distance;
   a receiver configured to receive a reflected portion of the ultrasonic wave that is reflected from the surface of the housing, in which the receiver is separated from the surface of the housing by a second distance; and
   processing logic coupled to the receiver, the processing logic configured to:
   sample the reflected portion of the ultrasonic wave at a sub-Nyquist rate in a zero-crossing region of the reflected portion of the ultrasonic wave to produce a set of samples;
   determine an amplitude of a frequency component of the set of samples; and
   to convert the amplitude of the frequency component into an amplitude of a vibration of the surface of the housing.

17. The system of claim 16, in which the processing logic includes an analog to digital converter configured to sample the reflected portion of the ultrasonic wave at a sub-Nyquist rate to produce the set of samples for use by the processing logic to determine the amplitude of the vibration of the surface of the housing, and in which the processing logic is further configured to convert the amplitude of the frequency component into an amplitude of vibration by calculating a phase shift displacement based on a wavelength of the reflected portion of the ultrasonic wave and a magnitude scale factor between a triangle approximation signal and the reflected portion of the ultrasonic wave in the zero crossing region.

* * * * *